(12) United States Patent
Lee et al.

(10) Patent No.: US 6,362,359 B1
(45) Date of Patent: Mar. 26, 2002

(54) ONE-COMPONENT THERMOSET COATING COMPOSITIONS

(75) Inventors: Sze-Ming Lee, Houston, TX (US); Karen M. Henderson, Coraopolis, PA (US); Patricia B. Jacobs, Pittsburgh, PA (US); Robert A. Sylvester, Carnegie, PA (US); Douglas A. Wicks, Lebanon, PA (US)

(73) Assignee: Bayer Corporation, Pittsburgh, PA (US)

( * ) Notice: Subject to any disclaimer, the term of this patent is extended or adjusted under 35 U.S.C. 154(b) by 0 days.

(21) Appl. No.: 09/727,630

(22) Filed: Dec. 1, 2000

(51) Int. Cl.$^7$ ................. C07C 281/02; C07C 271/06; C07C 271/08
(52) U.S. Cl. ................. 560/25; 428/413; 428/423.1; 428/447; 428/473.5; 428/474.4; 428/500; 428/524; 523/400; 523/402; 523/414; 523/415; 524/507; 524/555; 524/502; 524/588; 524/589; 524/590; 524/591; 524/600; 524/606; 524/608; 524/612; 524/831; 524/838; 524/843; 524/845; 524/869; 540/202; 525/123; 525/124; 525/329.4; 525/418; 525/454; 525/456; 525/474; 525/504; 525/509; 525/523; 525/528; 528/28; 528/45; 528/121; 528/123; 528/49; 528/119; 528/256; 528/259; 528/262; 528/263; 528/332; 528/335; 528/350; 528/407; 528/418; 528/421; 528/422; 560/26; 560/33; 560/115; 560/158; 560/159; 560/160; 560/165; 560/166; 564/35; 544/67; 544/68; 544/222; 548/951; 548/952; 548/953
(58) Field of Search ................. 524/845, 502, 524/507, 555, 588, 589, 590, 591, 600, 606, 608, 612, 831, 838, 843, 869; 523/400, 402, 414, 415; 525/523, 528, 123, 124, 329.4, 504, 509, 474, 418, 454, 456; 528/28, 45, 49, 256, 259, 262, 263, 407, 422, 332, 335, 350, 119, 121, 123, 421, 418; 560/26, 33, 25, 115, 158, 159, 160, 165, 166; 564/35; 540/202; 544/67, 68, 222; 548/951, 952, 953; 428/413, 423.1, 474.4, 500, 447, 473.5, 524

(56) References Cited

U.S. PATENT DOCUMENTS

| | | | | | |
|---|---|---|---|---|---|
| 3,585,200 | A | * | 6/1971 | Sheppard et al. | 544/388 |
| 3,594,231 | A | * | 7/1971 | Kraebel | 429/188 |
| 3,755,288 | A | * | 8/1973 | Sheppard et al. | 534/816 |
| 3,755,443 | A | * | 8/1973 | Sheppard et al. | 564/37 |
| 4,369,301 | A | * | 1/1983 | Konig et al. | 528/45 |
| 4,446,293 | A | * | 5/1984 | Konig et al. | 528/45 |
| 4,507,413 | A | * | 3/1985 | Thoma et al. | 524/42 |
| 6,060,573 | A | * | 5/2000 | Konig et al. | 528/45 |
| 6,127,514 | A | | 10/2000 | Wicks et al. | 528/367 |
| 6,150,457 | A | * | 11/2000 | Lee et al. | 525/123 |

FOREIGN PATENT DOCUMENTS

JP 47-49317 * 12/1972

* cited by examiner

Primary Examiner—Rabon Sergent
(74) Attorney, Agent, or Firm—Joseph C. Gil; Thomas W. Roy

(57) ABSTRACT

The present invention relates to compounds containing modified hydrazide groups and corresponding to formula I

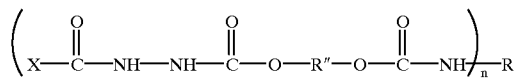

(I)

wherein

R represents the residue obtained by removing the isocyanate groups from a monomeric polyisocyanate, a polyisocyanate adduct or an NCO prepolymer, X represents OR' or NHR' and R' represents a group which is inert to isocyanate groups under the conditions used to form the compound of formula I, R" represents a divalent, linear or branched aliphatic group containing 2 to 10 carbon atoms, provided that there are at least two carbons between the oxygen atoms wherein the aliphatic group may optionally be substituted by heteroatoms to form ether or ester groups, and n is 2 to 6.

16 Claims, No Drawings

ONE-COMPONENT THERMOSET COATING COMPOSITIONS

BACKGROUND OF THE INVENTION

1. Field of the Invention

The present invention relates to polyisocyanate-based resins containing modified hydrazide groups, to one-component, thermoset compositions containing these resins and a cross-linking component and to their use for the production of coatings, sealants and adhesives.

2. Description of the Prior Art

One-component polyurethane coating compositions derived from polyisocyanates blocked with reversible, monofunctional blocking agents for isocyanate groups and polyols are an important class of material for applications such as automotive OEM coatings. While these one-component compositions overcome the difficulties of two-component coating compositions with regard to accurate metering of the components, the one-component coating compositions also have disadvantages, which are primarily caused by the volatilization of the blocking agent.

The release of the blocking agent can cause blistering and yellowing in thick films and oven fouling. In addition, the blocking agents are considered to be volatile organic compounds (VOC's) in the same manner as organic solvents. Therefore, certain coating compositions may not satisfy environmental regulations solely due to the presence of blocking agents.

These disadvantages of one-component coating compositions can be overcome in accordance with the invention described in U.S. Pat. No. 6,127,514 and in copending application, U.S. Ser. No. 09/197,912 now U.S. Pat. No. 6,150,457. Instead of using mixtures of polyols and polyisocyanates blocked with reversible, monofunctional blocking agents, the patent and application describe one-component compositions containing compounds containing modified hydrazide groups and cross-linking agents such as melamine resins. These compositions do not require blocking agents and, thus, do not release blocking agents during cure. When these coating compositions are cured, the only compounds-released are water or monoalcohols, which are much less toxic than conventional blocking agents.

In accordance with the preceding patent and application, the compounds containing modified hydrazide groups are prepared, e.g., by the reaction of polyisocyanates with alkyl carbazates such as ethyl carbazate. Examples of suitable polyisocyanates include NCO prepolymers, polyisocyanate adducts and monomeric polyisocyanates. One disadvantage is that the reaction products of polyisocyanate adducts or monomeric polyisocyanates with alkyl carbazates are gels or extremely viscous materials that have poor solubility in most common solvents.

It is an object of the present invention to prepare compounds containing modified hydrazide groups from polyisocyanates, especially monomeric polyisocyanates or polyisocyanate adducts, which are readily soluble in known organic solvents and which can be cured without the release of blocking agents. It is an additional object of the present invention to be able to obtain coatings that possess chemical stability, including acid etch resistance, which is comparable to that obtained from coatings prepared using blocked polyisocyanates as the crosslinking agent.

These objects can be achieved with the one-component compositions according to the present invention. In these compositions the compounds containing modified hydrazide groups are also modified with ester residues. When these compositions are cured, the only compounds released are water or monoalcohols.

SUMMARY OF THE INVENTION

The present invention relates to compounds containing modified hydrazide groups and corresponding to formula I

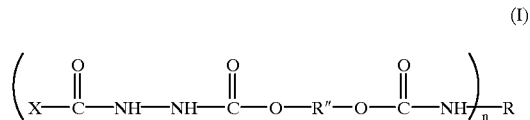

wherein

R represents the residue obtained by removing the isocyanate groups from a monomeric polyisocyanate, a polyisocyanate adduct or an NCO prepolymer, X represents OR' or NHR' and R' represents a group which is inert to isocyanate groups under the conditions used to form the polyurethane of formula I, R" represents a divalent, linear or branched aliphatic group containing 2 to 10 carbon atoms, provided that there are at least two carbons between the oxygen atoms, wherein the aliphatic group may optionally be substituted by heteroatoms to form ether or ester groups, and n is 2to 6.

The present invention also relates to one-component, thermoset compositions containing the compounds of formula I and a cross-linking component that is reactive with these compounds. Finally, the present invention relates coatings, sealants and adhesives prepared from these thermoset compositions.

DETAILED DESCRIPTION OF THE INVENTION

The compounds of formula I are preferably prepared by reacting a polyisocyanate, R—(NCO)$_n$, with a compound corresponding to formula II

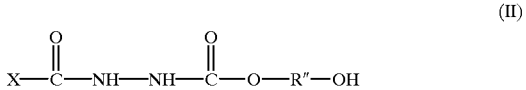

wherein X, R' and R" are as previously defined.

The compounds corresponding to formula II may be prepared by reacting a compound corresponding to formula III

with a cyclic carbonate as described in U.S. Pat. No. 4,369,301. Suitable cyclic carbonates include ethylene carbonate, 1,2-propylene carbonate, 1,3-propylene carbonate and neopentyl carbonate. Ethylene carbonate and 1,2-propylene carbonate are preferred, and 1,2-propylene carbonate is especially preferred.

It is also possible to prepare the compounds of formula II by reacting the compounds of formula III with chloroformate hydroxyesters corresponding to formula (IV)

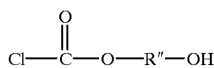

(IV)

This method is suitable for preparing the compounds of formula II from compounds which cannot be converted into cyclic carbonates.

In formulas I, II, III and IV

X represents OR' or NHR', preferably OR', and

R' represents a group which is inert to isocyanate groups under the conditions used to form the compound of formula I, preferably an alkyl, cycloalkyl, araliphatic or aromatic group containing 1 to 20, preferably 1 to 10 carbon atoms, which may optionally be substituted by heteroatoms to form ether or ester groups, R" represents a divalent, linear or branched aliphatic group containing 2 to 10 carbon atoms, provided that there are at least two carbons between the oxygen atoms, wherein the aliphatic group may optionally be substituted by heteroatoms to form ether or ester groups, preferably a linear or branched alkylene group having 2 to 5 carbon atoms, n is 2 to 6, preferably 2 to 4.

When X represents OR', examples of R' include methyl, ethyl, propyl, butyl, hexyl, octyl, phenyl, cyclohexyl and benzyl. Most preferably, R' is an alkyl group having 1 to 4 carbon atoms. When X represents NHR, R' is most preferably an alkyl group containing at least 4 carbon atoms.

Compounds corresponding to formula III wherein X represents NHR' can be prepared by reacting hydrazine with an organic monoisocyanate in a molar ratio of 1:1.In order to increase the amount of product corresponding to formula III, it is also possible to use an excess amount of hydrazine and to remove the excess, e.g., by precipitation, distillation or extraction. However, this is generally not necessary since the selectivity to form the monoadduct is very high.

Examples of suitable polyisocyanates which may be used as the polyisocyanate component to prepare the compounds of formula I include monomeric polyisocyanates, polyisocyanate adducts and NCO prepolymers having an average functionality of 1.5 to 6, preferably 1.8 to 6, more preferably 2 to 6 and most preferably 2 to 4. Monomeric polyisocyanates and polyisocyanate adducts are preferred.

Suitable monomeric diisocyanates may be represented by the formula

in which R represents an organic group obtained by removing the isocyanate groups from an organic diisocyanate having a molecular weight of about 112 to 1,000, preferably about 140 to 400. Preferred diisocyanates for the process according to the invention are those represented by the above formula in which R represents a divalent aliphatic hydrocarbon group having 4 to 40, preferably 4 to 18 carbon atoms, a divalent cycloaliphatic hydrocarbon group having 5 to 15 carbon atoms, a divalent araliphatic hydrocarbon group having 7 to 15 carbon atoms or a divalent aromatic hydrocarbon group having 6 to 15 carbon atoms.

Examples of suitable organic diisocyanates include 1,4-tetramethylene diisocyanate, 1,6-hexamethylene diisocyanate, 2,2,4-trimethyl-1,6-hexamethylene diisocyanate, 1,12-dodecamethylene diisocyanate, cyclohexane-1,3- and -1,4-diisocyanate, 1-isocyanato-2-isocyanatomethyl cyclopentane, 1-isocyanato-3-isocyanatomethyl-3,5,5-trimethyl-cyclohexane (isophorone diisocyanate or IPDI), bis-(4-isocyanatocyclohexyl)-methane, 2,4'-dicyclohexyl-methane diisocyanate, 1,3-and 1,4-bis-(isocyanatomethyl)-cyclohexane, bis-(4-isocyanato-3-methyl-cyclohexyl)-methane, α, α, α', α'-tetramethyl-1,3- and/or -1,4-xylylene diisocyanate, 1-isocyanato-1-methyl-4(3)-isocyanatomethyl cyclohexane, 2,4- and/or 2,6-hexahydrotoluylene diisocyanate, 1,3- and/or 1,4-phenylene diisocyanate, 2,4- and/or 2,6-toluylene diisocyanate, 2,4- and/or 4,4'-diphenyl-methane diisocyanate, 1,5-diisocyanato naphthalene and mixtures thereof.

Polyisocyanates containing 3 or more isocyanate groups such as 4-isocyanatomethyl-1,8-octamethylene diisocyanate and aromatic polyisocyanates such as 4,4',4"-triphenylmethane diisocyanate and polyphenyl polymethylene polyisocyanates obtained by phosgenating aniline/formaldehyde condensates may also be used.

Preferred organic diisocyanates include 1,6-hexamethylene diisocyanate, 1-isocyanato-3-isocyanatomethyl-3,5,5-trimethyl-cyclohexane (isophorone diisocyanate or IPDI), bis-(4-isocyanato-cyclohexyl)-methane, 1-isocyanato-1-methyl4(3)-isocyanatomethyl cyclohexane, 2,4- and/or 2,6-toluylene diisocyanate, and 2,4- and/or 4,4'-diphenyl-methane diisocyanate.

In accordance with the present invention the polyisocyanate component may be in the form of a polyisocyanate adduct. Suitable polyisocyanate adducts are those containing isocyanurate, uretdione, biuret, urethane, allophanate, iminooxadiazine dione, carbodiimide and/or oxadiazine-trione groups. The polyisocyanates adducts have an average functionality of 2 to 6 and an NCO content of 5 to 30% by weight and include:

1) Isocyanurate group-containing polyisocyanates which may be prepared as set forth in DE-PS 2,616,416, EP-OS 3,765, EP-OS 10,589, EP-OS 47,452, U.S. Pat. No. 4,288,586 and U.S. Pat. No. 4,324,879. The isocyanato-isocyanurates generally have an average NCO functionality of 3 to 3.5 and an NCO content of 5 to 30%, preferably 10 to 25% and most preferably 15 to 25% by weight.

2) Uretdione diisocyanates which may be prepared by oligomerizing a portion of the isocyanate groups of a diisocyanate in the presence of a suitable catalyst, e.g., a trialkyl phosphine catalyst, and which may be used in admixture with other aliphatic and/or cycloaliphatic polyisocyanates, particularly the isocyanurate group-containing polyisocyanates set forth under (1) above.

3) Biuret group-containing polyisocyanates which may be prepared according to the processes disclosed in U.S. Pat. Nos. 3,124,605; 3,358,010; 3,644,490; 3,862,973; 3,903,126; 3,903,127; 4,051,165; 4,147,714; or4,220, 749 by using co-reactants such as water, tertiary alcohols, primary and secondary monoamines, and primary and/or secondary diamines. These polyisocyanates preferably have an NCO content of 18 to 22% by weight and an average NCO functionality of 3 to 3.5.

4) Urethane group-containing polyisocyanates which may be prepared in accordance with the process disclosed in U.S. Pat. No. 3,183,112 by reacting excess quantities of polyisocyanates, preferably diisocyanates, with low molecular weight glycols and polyols having molecular weights of less than 400, such as trimethylol propane, glycerine, 1,2-dihydroxy propane and mixtures thereof. The urethane group-containing polyisocyanates have a most preferred NCO content of 12 to 20% by weight and an (average) NCO functionality of 2.5 to 3.

5) Allophanate group-containing polyisocyanates which may be prepared according to the processes disclosed in U.S. Pat. Nos. 3,769,318, 4,160,080 and 4,177,342, and copending application, U.S. Ser. No. 08/432,285. The allophanate group-containing polyisocyanates have a most preferred NCO content of 12 to 21% by weight and an (average) NCO functionality of 2 to 4.5. Preferred catalysts for the preparation of these polyisocyanates include organic tin(II) salts such as tin(II) octoate.

6) Isocyanurate and allophanate group-containing polyisocyanates which may be prepared in accordance with the processes set forth in U.S. Pat. Nos. 5,124,427, 5,208,334, 5,235,018 and 5,444,146, the disclosures of which are herein incorporated by reference, preferably polyisocyanates containing these groups in a ratio of monoisocyanurate groups to monoallophanate groups of about 10:1 to 1:10, preferably about 5:1 to 1:7.

7) Iminooxadiazine dione and optionally isocyanurate group-containing polyisocyanates which may be prepared in the presence of special fluorine-containing catalysts as described in DE-A 19611849. These polyisocyanates generally have an average NCO functionality of 3 to 3.5 and an NCO content of 5 to 30%, preferably 10 to 25% and most preferably 15 to 25% by weight.

8) Carbodiimide group-containing polyisocyanates which may be prepared by oligomerizing di- or polyisocyanates in the presence of known carbodiimidization catalysts as described in DE-PS 1,092,007, U.S. Pat. No. 3,152,162 and DE-OS 2,504,400, 2,537,685 and 2,552,350.

9) Polyisocyanates containing oxadiazinetrione groups and containing the reaction product of two moles of a diisocyanate and one mole of carbon dioxide.

Preferred polyisocyanate adducts are the polyisocyanates containing isocyanurate, uretdione, biuret, iminooxadiazine dione and/or allophanate groups.

The NCO prepolymers, which may also be used as the polyisocyanate component to prepare the compounds of formula I, are prepared from the previously described monomeric polyisocyanates or polyisocyanate adducts, preferably monomeric diisocyanates, and organic compounds containing at least two isocyanate-reactive groups, preferably at least two hydroxy groups. These organic compounds include high molecular weight compounds having molecular weights of 400 to about 6,000, preferably 800 to about 3,000, and optionally low molecular weight compounds with molecular weights below 400. The molecular weights are number average molecular weights ($M_n$) and are determined by end group analysis (OH and/or NH number). Products obtained by reacting polyisocyanates exclusively with low molecular weight compounds are polyisocyanates adducts containing urethane groups and are not considered to be NCO prepolymers.

Examples of the high molecular weight compounds are polyester polyols, polyether polyols, polyhydroxy polycarbonates, polyhydroxy polyacetals, polyhydroxy polyacrylates, polyhydroxy polyester amides and polyhydroxy polythioethers. The polyester polyols, polyether polyols and polyhydroxy polycarbonates are preferred, while the polyester polyols and polyhydroxy polycarbonates are more preferred.

Examples of suitable high molecular weight polyhydroxyl compounds include polyester polyols prepared from low molecular weight alcohols and polybasic carboxylic acids such as adipic acid, sebacic acid, phthalic acid, isophthalic acid, tetrahydrophthalic acid, hexahydrophthalic acid, maleic acid, the anhydrides of these acids and mixtures of these acids and/or acid anhydrides. Polylactones having hydroxyl groups, particularly poly-ε-caprolactone, are also suitable for producing the prepolymers.

Also suitable for preparing the NCO prepolymers are polyether polyols, which may be obtained in known manner by the alkoxylation of suitable starter molecules. Examples of suitable starter molecules include polyols, water, organic polyamines having at least two N-H bonds and mixtures thereof. Suitable alkylene oxides for the alkoxylation reaction are preferably ethylene oxide and/or propylene oxide, which may be used in sequence or in admixture.

Other suitable polyols include polycarbonates having hydroxyl groups, which may be produced by the reaction of diols with phosgene or diaryl carbonates such as diphenyl carbonate.

Further details concerning the low molecular weight compounds and the starting materials and methods for preparing the high molecular weight polyhydroxy compounds are disclosed in U.S. Pat. No. 4,701,480, herein incorporated by reference.

Other examples include the known high molecular weight amine-functional compounds, which may be prepared by converting the terminal hydroxy groups of the polyols previously described to amino groups, and the high molecular weight polyaspartates and polyaldimines disclosed in U.S. Pat. Nos. 5,243,012 and 5,466,771, respectively, herein incorporated by reference. A particular advantage for the use of polyaspartates to prepare the isocyanate addition products is that during the subsequent curing of these products the urea groups react to form thermally stable hydantoin groups.

The NCO prepolymers generally have an isocyanate content of 0.4 to 20% by weight, preferably 0.4 to 15% by weight and more preferably 0.5 to 10.0% by weight. The NCO prepolymers are prepared in known manner by the reaction of the above mentioned starting materials at a temperature of 40 to 120° C., preferably 50 to 100° C. and at an NCO/OH (or NH) equivalent ratio of about 1.3:1 to 20:1 preferably about 1.4:1 to 10:1. If chain extension via urethane groups is desired during the preparation of the isocyanate prepolymers, an NCO/OH equivalent ratio of 1.3:1 to 2:1 is selected. If chain extension is not desired, an excess of diisocyanate is preferably used, corresponding to an NCO/OH equivalent ratio of 4:1 to 20:1, preferably 5:1 to 10:1. The excess diisocyanate (and any volatile solvent used during the preparation) may optionally be removed by thin layer distillation when the reaction is completed. In accordance with the present invention NCO prepolymers also include NCO semi-prepolymers which contain unreacted starting polyisocyanates in addition to the urethane group-containing prepolymers.

The compounds containing modified hydrazide groups may be prepared by reacting the polyisocyanates with the compounds corresponding to formula II at a temperature of 20 to 150° C., preferably 50 to 100° C. The amount of the compounds corresponding to formula II should be sufficient to react with all or substantially all (i.e., up to 90 equivalent %), preferably all, of the isocyanate groups of the polyisocyanate.

To prepare the one-component, thermoset compositions the compounds of formula I are blended with a compound that is reactive with the modified hydrazide functional groups. These reactive groups include active methylol or methylalkoxy groups on aminoplast crosslinking agents or on other compounds such as phenol/formaldehyde adducts, siloxane or silane groups and anhydride groups. Also suitable are the compounds containing epoxy groups, preferably two or more epoxy groups, which are described in U.S. Pat. No. 6,127,514, herein incorporated by reference.

Examples compounds containing active methylol or methylalkoxy groups include melamine formaldehyde resins (including monomeric or polymeric melamine resins and partially or fully alkylated melamine resins), urea resins (e.g., methylol ureas such as urea formaldehyde resins and alkyoxy ureas such as butylated urea formaldehyde resins), N-methylol acrylamide emulsions, isobutoxy methyl acrylamide emulsions, polyanhydrides (e.g., polysuccinic anhydride), and siloxanes or silanes (e.g., dimethyldimethoxy silane). Preferred are aminoplast resins such as melamine formaldehyde resins or urea formaldehyde resins.

To control the crosslink density of the final product, it is possible to react off one or more of the amino nitrogens or hydroxy groups. For example, alkylated melamine/formaldehyde or urea/formaldehyde resins can be reacted with a compound corresponding to the formula

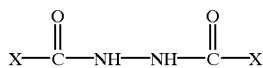

wherein X and R' are as defined above.

In the one-component, thermoset compositions according to the invention the compounds corresponding to formula I and the coreactants should preferably be present in an amount sufficient to provide an equivalent ratio of modified hydrazide groups to the groups that are reactive with the modified hydrazide groups of 2:1 to 1:6, more preferably 1.5:1 to 1:3, most preferably 1.2:1 to 1:2.5. When aminoplast resins, especially melamine resins, are used, they may be present in an amount of 10 to 70%, based on weight of the reactive components. This amount is higher than the above equivalent ratios, since these resins may also undergo self-crosslinking.

When aminoplast compounds, especially monomeric melamines are used as the co-reactant for the compounds of formula I, strong acid catalysts are preferred. These catalysts are well known and include p-toluenesulfonic acid, dinonylnaphthalene disulfonic acid, dodecylbenzene-sulfonic acid, phenyl acid phosphate, monobutyl maleate, butyl phosphate and hydroxy phosphate ester. Other catalysts that may be useful include Lewis acids, zinc salts and tin salts.

The one-component compositions may contain the organic solvents known from melamine chemistry. These solvents may be present in an amount of up to 95%, preferably up to 80%, based on the total weight of the thermoset composition. Alcohols may be added to improve shelf stability.

It is also possible in accordance with the subject application to use water as the solvent. If the thermoset compositions are dispersed in water, the reactants preferably have a hydrophilic character, which may be obtained in known manner by incorporating ionic and/or non-ionic hydrophilic groups into the reactants and/or by the use of external emulsifiers.

The one-component, thermoset compositions of the present invention are suitable for preparing coatings, adhesives or sealants. Depending upon the particular application the compositions may also contain known additives, such as leveling agents, wetting agents, flow control agents, antiskinning agents, antifoaming agents, fillers (such as silica, aluminum silicates and high-boiling waxes), viscosity regulators, plasticizers, pigments, dyes, UV absorbers and stabilizers against thermal and oxidative degradation.

The one-component compositions may be applied to any heat resistant substrates, preferably metals, glass and ceramics, and more preferably metals. They may be applied by standard methods, such as spray coating, spread coating, flood coating, casting, dip coating, roll coating. The coating compositions may be clear or pigmented.

The one-component, thermoset compositions are cured at elevated temperatures of 80 to 250° C., preferably 100 to 230° C. and more preferably 100 to 160° C., for a period of 5 to 60 minutes, preferably 10 to 50 minutes and more preferably 20 to 40 minutes.

The invention is further illustrated, but is not intended to be limited by the following examples in which all parts and percentages are by weight unless otherwise specified.

EXAMPLES

The Following Starting Materials were used in the Examples

Polyisocyanate 1

An isocyanurate group-containing polyisocyanate present as a 70% solution in 2:1 blend of solvent naphtha 100 and butyl acetate, prepared from isophorone diisocyanate, and having, based on the weight of the solution, an isocyanate content of 11.7% by weight, a content of monomeric diisocyanate of <0.5% and a viscosity at 20° C. of 1300 to 2700 mPa.s (available from Miles Inc. as Desmodur Z 4470 SN/BA).

Polyisocyanate 2

A polyisocyanate which contains allophanate groups and isocyanurate groups, is prepared from 1,6-hexamethylene diisocyanate and has an isocyanate content of 20.3%, a content of monomeric diisocyanate of <0.2% and a viscosity at 25° C. of about 1100 mPa≈s (available from Bayer Corporation as Desmodur XP-7100).

Polyisocyanate 3

A polyisocyanate containing isocyanurate and iminooxadiazine dione groups, having an isocyanate content of about 23% and prepared from 1,6-hexamethylene diisocyanate in accordance with U.S. Pat. No. 5,914,383.

Polyisocyanate 4

A biuret group-containing polyisocyanate prepared from 1,6-hexamethylene diisocyanate and having an isocyanate content of about 23%, a content of monomeric diisocyanate of <0.7% and a viscosity at 25° C. of 1300–2200 mPa.s (available from Miles Inc. as Desmodur N 3200).

Compound of formula II 324 parts of propylene carbonate were heated at 60° C. under nitrogen in a 1 liter, 3-necked flask fitted with mechanical stir and water condenser. 330 parts of ethyl carbazate were melted and poured into the reaction flask over 30 minutes. The mixture was stirred at 110° C. for 48 h. Afterwards, the crude product was purified by distilling off the unreacted starting materials and side products at 100° C. and 1 Torr pressure.

Examples 1–8

General Procedure for Preparing the Modified Hydrazides of Formula I

The isocyanate (0.78 equiv.) was dissolved in 50 parts of methyl isobutyl ketone (MIBK) in a 500 ml, 3-necked round bottom flask. The solution was stirred at 90° C. The compound of formula II (0.76 equiv.) was heated to 100° C. and added to the isocyanate solution. The mixture was stirred at 110° C. for 24 h. A second potion of MIBK was then added to give a 60% solids solution. The results are set forth in Table 1.

Comparison Examples 9–13
General Procedure for Preparing Unmodified Hydrazides

The isocyanate (0.78 mole equivalent) was dissolved in MIBK as a 60% solids solution in a 500 ml, 3-necked round bottom flask. The solution was stirred at 60° C. Ethyl carbazate (0.76 mole equivalent) was dissolved in MIBK to prepare a 60% solids solution. The ethyl carbazate solution was heated to 60° C. and added dropwise into the isocyanate solution. The resulting products were viscous, non-flowable oils having a viscosity in excess of 1,000,000 mPa.s (the upper limit of the Brookfield viscometer used to determine viscosity). The products and solvent separated into two phases. The results are set forth in Table 1.

TABLE 1

| | Unmodified hydrazides | | Modified hydrazides | |
|---|---|---|---|---|
| Isocyanate | Example | Product viscosity @ 25° C./mPa.s | Comp. Example | Product viscosity @ 25° C./mPa.s |
| IPDI | 1 | 8400 | 9 | Thick oil |
| Polyiso 1 | 2 | 107000 | 10 | Thick oil |
| Polyiso 2 | 3 | 5200 | 11 | Thick oil |
| Polyiso 3 | 4 | 6700 | 12 | Thick oil |
| Polyiso 4 | 5 | 8200 | 13 | Thick oil |
| IPDI + Polyiso 2 (1:1 wt. ratio) | 6 | 3100 | | |
| IPDI + HDI (1:1 wt. Ratio) | 7 | 1300 | | |
| IPDI + HDI + Polyiso 2 (2:2:1 wt. ratio) | 8 | 1500 | | |

These results demonstrate the improvement in viscosity obtained for the compounds of formula I when compared to the compounds prepared in comparison examples 9–13.

Example 14

A coating composition was prepared from 30 parts of the product of Example 3, 5.8 parts of methoxylated hexamethylol melamine (Resimene 747, Solutia), 8 parts of propylene glycol monomethyl ether acetate (PMA) and 2.4 parts of a 10% solution of p-toluenesulfonic acid in isopropanol. The composition was drawn down onto a rolled steel panel with a 5 mil drawdown bar and baked at 130° C. for 30 min. The resulting coating was clear and insoluble in acetone.

Example 15

A coating composition was prepared from 26 parts of the product of Example 6, 5.8 parts of methoxylated hexamethylol melamine (Resimene 747, Solutia), 8 parts of PMA and 2.4 parts of a 10% solution of p-toluenesulfonic acid in isopropanol. The composition was drawn down onto a rolled steel panel with a 5 mil drawdown bar and baked at 130° C. for 30 min. The resulting coating was clear and insoluble in acetone.

Comparison Example 16
Reaction of Ethyl Carbazate with Caprolactone 500 g of ε-caprolactone (4.4 moles) were placed in a 2 liter, round-bottomed flask. 456 g of ethyl carbazate (4.4 moles) were melted at 60° C. and then added to the c-caprolactone. The mixture was stirred at 110° C. for 24 h. The unreacted starting materials were removed by vacuum distillation.

Reaction of Isocyanate with the Reaction Product of Ethyl Carbazate and ε-Caprolactone IPDI (1 equiv.) was dissolved in PMA to prepare a 60% solids solution and stirred at 90° C. in a round-bottomed flask. The reaction product of ethyl carbazate and caprolactone was dissolved in PMA (60% solid) and added to the isocyanate solution. The mixture was stirred at 90° C. for 24 hours. The resulting product remained soluble in PMA.

A coating composition was prepared from 15 parts of this product, 5.8 parts of methoxylated hexamethylol melamine (Resimene 747, Solutia), 8 parts of PMA and 2.4 parts of a 10% solution of p-toluenesulfonic acid in isopropanol. The composition was drawn down onto a rolled steel panel with a 5 mil drawdown bar and baked at 130° C. for 30 min. The resulting coating was readily dissolved by acetone, indicating that no crosslinking occurred during cure.

This example demonstrates the criticality of using the compounds of formula II to prepare the modified hyrazide groups of the present invention.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A compound containing modified hydrazide groups and corresponding to formula I

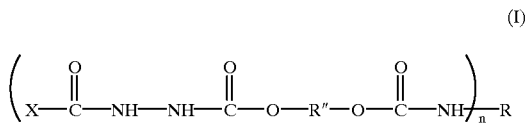

wherein
R represents the residue obtained by removing the isocyanate groups from a monomeric polyisocyanate, a polyisocyanate adduct or an NCO prepolymer,
x represents OR' or NHR',
R' represents a group which is inert to isocyanate groups under the conditions used to form the compound of formula I,
R" represents a divalent, linear or branched aliphatic group containing 2 to 10 carbon atoms, provided that there are at least two carbons between the oxygen atoms present on either side of R" in formula I, wherein the aliphatic group is optionally substituted by heteroatoms to form ether or ester groups, and
n is 2 to 6.
2. The compound of claim 1 wherein
R' represents an alkyl group containing 1 to 10 carbon atoms.
3. The compound of claim 1 wherein
X represents OR'.
4. The compound of claim 2 wherein
X represents OR'.
5. The compound of claim 1 wherein
R represents the residue obtained by removing the isocyanate groups from a monomeric polyisocyanate or a polyisocyanate adduct.

6. The compound of claim 2 wherein
R represents the residue obtained by removing the isocyanate groups from a monomeric polyisocyanate or a polyisocyanate adduct.

7. The compound of claim 3 wherein
R represents the residue obtained by removing the isocyanate groups from a monomeric polyisocyanate or a polyisocyanate adduct.

8. The compound of claim 4 wherein
R represents the residue obtained by removing the isocyanate groups from a monomeric polyisocyanate or a polyisocyanate adduct.

9. The compound of claim 1 wherein
R" represents a divalent, linear or branched aliphatic group having 2 to 5 carbon atoms and
n is 2 to 4.

10. The compound of claim 2 wherein
R" represents a divalent, linear or branched aliphatic group having 2 to 5 carbon atoms and
n is 2 to 4.

11. The compound of claim 3 wherein
R" represents a divalent, linear or branched aliphatic group having 2 to 5 carbon atoms and
n is 2 to 4.

12. The compound of claim 4 wherein
R" represents a divalent, linear or branched aliphatic group having 2 to 5 carbon atoms and
n is 2 to 4.

13. The compound of claim 5 wherein
R" represents a divalent, linear or branched aliphatic group having 2 to 5 carbon atoms and
n is 2 to 4.

14. The compound of claim 6 wherein
R" represents a divalent, linear or branched aliphatic group having 2 to 5 carbon atoms and
n is 2 to 4.

15. The compound of claim 7 wherein
R" represents a divalent, linear or branched aliphatic group having 2 to 5 carbon atoms and
n is 2 to 4.

16. The compound of claim 8 wherein
R" represents a divalent, linear or branched aliphatic group having 2 to 5 carbon atoms and
n is 2 to 4.

* * * * *